United States Patent [19]

Mattes et al.

[11] Patent Number: 4,591,572

[45] Date of Patent: May 27, 1986

[54] PIGMENTATION ASSOCIATED, DIFFERENTIATION ANTIGEN OF HUMAN MELANOMA AND AUTOLOGOUS ANTIBODY

[75] Inventors: M. Jules Mattes, Jamaica Estates; Timothy M. Thomson; Lloyd J. Old, both of New York; Kenneth O. Lloyd, Bronx, all of N.Y.

[73] Assignee: Sloan-Kettering Institute for Cancer Research, New York, N.Y.

[21] Appl. No.: 481,379

[22] Filed: Apr. 1, 1983

[51] Int. Cl.[4] ............................................. G01N 33/54
[52] U.S. Cl. ..................... 436/538; 436/539; 436/542; 436/543; 436/544; 436/545; 436/547; 436/804; 436/811; 436/813; 436/815; 436/823; 436/828; 530/387; 530/806; 424/1.1; 424/85; 424/88; 435/7; 435/948
[58] Field of Search ................. 436/536-547, 436/804, 813, 518, 528, 548, 811, 815, 823, 828; 435/4, 7, 259, 948; 424/1.1, 9, 85, 88, 177; 260/112 R; 23/915

[56] References Cited

U.S. PATENT DOCUMENTS

| | | | |
|---|---|---|---|
| 4,017,471 | 4/1977 | Davies | 260/112 B |
| 4,172,124 | 10/1979 | Koprowski | 424/85 |
| 4,331,647 | 5/1982 | Goldenberg | 424/1.1 |
| 4,361,544 | 11/1982 | Goldenberg | 424/9 |
| 4,414,148 | 11/1983 | Jansen et al. | 260/112 B |

OTHER PUBLICATIONS

Heaney-Kieras, J. et al., Cancer Research, vol. 42, pp. 2310-2316, (1982).
Mattes, M. J. et al., Int. J. Cancer, vol. 32, pp. 717-721, (1983).
Natali, P. G. et al., Cancer Research, vol. 42, pp. 583-589, (2-1982).
Seiji, M., Pigment Cell Biology, vol. 117 (10), pp. 845-852, (1981) (Japanese).
Carey, T. E. et al., Proc. Natl. Acad. Sci., USA (Wash.), vol. 73, pp. 3278-3282, (1976).
Howanitz, N. et al., Arch. Dermatol., vol. 117, pp. 705-708, (1981).
Nishioka, K. et al., Europ. J. Biochem., vol. 85, pp. 137-146, (1978).
Hearing, V. J. et al., Int. J. Biochem., vol. 13, pp. 99-103, (1981).
Tai, T. et al., Cancer Research, vol. 43(6), pp. 2773-2779, (6-1983).
Carey, T. E. et al., Proc. Natl. Acad. Sci., USA, vol. 76(6), pp. 2898-2902, (1979).
Hoefs, T., Folia Haematol, vol. 109(2), pp. 244-250, (1982) (German).
Hakim, A. A. et al., Immunology Letters, vol. 4, pp. 59-64, (1982).
Carey et al., Proc. Nat'l. Acad. Sci., U.S.A., vol. 73, No. 9, pp. 3278-3282, (Sep. 1976).

*Primary Examiner*—Thomas G. Wiseman
*Assistant Examiner*—M. Moskowitz
*Attorney, Agent, or Firm*—Felfe & Lynch

[57] ABSTRACT

The present invention concerns an autologous precipitating antibody and the gp70 pigment-associated antigen on melanoma cells which it recognizes. The antibody is useful in detecting pigmented melanoma cells in excised specimen, serum or urine.

14 Claims, No Drawings

CHARACTERIZATION OF PAA ANTIGEN AND PRECIPITATING AUTOANTIBODIES

Antibodies were found in serum from a melanoma patient, AU, that precipitate an antigen, of molecular weight 70,000, form an $^{125}$I-labeled NP40 solubilized preparation from the autologous tumor cell line SK-MEL-28. These precipitating antibodies were absorbed by SK-MEL-28 cells but not by cells from another melanoma, SK-MEL-37. Additional absorptions were performed to determine the distribution of this antigen. Eight of 15 melanomas absorbed and antibodies and 17 other cell types were negative, including 3 astrocytomas, 3 ovarian carcinomas, 1 uterine carcinoma, 2 bladder carcinomas, 1 renal carcinoma, 2 lung carcinomas, 1 breast carcinoma, 1 colon carcinoma, 1 choriocarcinoma, 1 leukemia and human erythrocytes.

A positive absorption among melanoma cell lines was associated, without exception, with pigmentation of the cell lines. To further examine this relationship, quantitative absorptions were performed with 2 cell lines: SK-MEL-28, a lightly pigmented cell lines, and SK-MEL-23, a very highly pigmented cell line. Results demonstrate that SK-MEL-23 is approximately 30 times more effective than SK-MEL-23 at absorbing these antibodies. This experiment was repeated with a second very highly pigmented melanoma (SK-MEL-21), with similar results, with 2 astrocytomas showed negative absorption. Therefore, and the correlation of antigen expression with pigmentation was confirmed. This antigen was therefore designated pigmentation associated antigen (PAA). PAA is distinct from melanin itself which is not solubilized under the conditions employed.

Iodinated antigen preparations from two other lines, the highly pigmented SK-MEL-23 and the non-pigmented SK-MEL 37 were also observed. AU serum precipitated nothing from labeled SK-MEL-37 but precipitated a component corresponding to PAA from labelled SK-MEL-23, and the band seen was much stronger than that seen with labeled SK-MEL-28. This experiment further supports the correlation of PAA expression with degree of pigmentation of the cell line.

Also, PAA was precipitated from iodinated antigen preparations from normal human melanocytes, indicating that it is a normal differentation marker.

SK-MEL-28 melanoma cells labeled by [$^{35}$S]methionine or [$^{3}$H]glucosamine had previously been examined for the presence of an antigen that precipitates with autologous serum, and no precipitated antigen was detected. Since $^{125}$I labeling, in contrast to biosynthetic labeling methods, will label components of the fetal calf serum included in tissue culture medium, it is important to exclude the possibility that the antigen is a heterologous component derived from the serum. Immune precipitation was not inhibited by a large excess of unlabeled fetal calf serum. Also, a Con A eluate fraction of fetal calf serum was labeled with $^{125}$I and tested in immune precipitation with serum AU: no component resembling PAA was precipitated. Therefore, we conclude that PAA probably is a biosynthetic product of the tumor cells.

Other characteristics of PAA have been determined. Unreduced samples migrated at the same rate as reduced samples on SDS-acrylamide gels. The isoelectric point is at pI 5.2, with a second minor spot at pI 5.5. The antigen binds to Concanavalin A-Sepharose and is eluted with methyl-a-D-mannoside. A fraction (10-25%) also binds to wheat germ agglutinin and is eluted with N-acetyl-glucosamine. A similar fraction binds to *Ricinus communis* lectin-I and is eluted with D-galactose. PAA did not bind to the other lectins tested, (lentil lectin, peanut agglutinin, soybean agglutinin, and lectins from *Bandeira simplicifolia, Helix pomatia* and *Lotus tetragonolobus*).

The frequency of antibodies to PAA was investigated by screening 96 sera samples from melanoma patients using the same precipitating method with $^{125}$I-labeled SK-MEL-28. Fifteen $\mu$l of each serum was tested, while 3 l of AU serum has been used routinely. None of the sera precipitated PAA. A smaller number of normal human sera were also tested and found to be negative. Precipitating antibodies were found in approximately 10% of these sera, but the antigens recognized were diverse and different from the 70K antigen.

It is critical in these experiments that the antigen preparation be in $^{125}$I-labeled eluate fraction from a Concanavalin A-Sepharose column of an NP-40-solubilized whole cell extract. When the same experiments were performed with an iodinated solubilized crude membrane preparation, no precipitation was seen. This emphasizes the fact that variation in sample composition can be critical in determining whether or not a particular antigen is detected. Moreover, no specific components were precipitated by the serum from lysates of cells metabolically labeled with [$^{35}$S]methionine a [$^{3}$H]glucosamine. Sensitivity for detecting a particular antigen would seem to depend on the efficiency of labeling that particular molecule relative to other cell constituents, to the amount of radioactivity used for each sample in immune precipitation, to the background seen on acrylamide gels due to nonspecific sticking to the immunoabsorbent, *Staphylococcus aureus*, and to the film exposure time. The antigen identified is a differentiation antigen closely correlated with pigmentation, highly pigmented melanomas express more PAA than do lightly pigmented melanomas. PAA was undetectable in non-pigmented melanomas and other tumor cell types.

Other melanocyte differentiation markers share some properties with PAA, but seem to be distinct. Tyrosinase, the major enzyme involved in melanin production, is a glycoprotein of approximately 75,000 dalton. But an antiserum that reacts with human tyrosinase, did not precipitate PAA.

Antibodies to other melanocyte differentiation antigens have been found in human sera. The Mel 1 antigen, detected on normal melanocytes and fetal fibroblasts but absent from adult fibroblasts, normal kidney epithelial cells, and EB virus-transformed B cells, was recognized by IgG antibodies in 1 serum sample of 106 normal male sera tested. The AH antigen is present on most melanomas and astrocytomas but absent from carcinomas, fibroblasts and EB-virus-transformed B cell lines. These two antigens are clearly distinct from PAA, but the mechanism of induction of such antibodies may be similar.

Antibodies in the serum of melanoma patient AU precipitate an antigen from $^{125}$I-labeled extracts of cultured autologous melanoma cells. The antigen is present in other pigmented melanomas but not in non-pigmented melanomas or other tumor cell types, and the amount of antigen is correlated with the degree of pigmentation. These conclusions are based on absorption experiments with 11 pigmented melanomas, 8 non-pigmented melanomas, 3 astrocytomas, 12 carcinomas of various histological types, 1 leukemia and human erythrocytes. The antigen has a molecular weight of 70,000 and isoelectric point of pH 5.3. It binds to Concanavalin A-Sepharose. Ninety-six other melanoma sera were examined and none of them precipitated this antigen. The serum from patient AU also has antibodies to a unique (Class 1) tumor antigen found only on AU melanoma cells. The pigmentation-associated, differentiation antigen and the unique autologous antigen are clearly different in their distribution, but some relationship between these unusual antibody responses is possible.

We claim:

1. Substantially pure antibody which specifically binds to the pigmentation-associated gp70 antigen specific to melanocytes and melanomas, said antigen having an isoelectric point of 5.2.

2. Antibody of claim 1 labelled with a radioactive or chromophoric group.

3. Antibody of claim 1 immobilized on a solid inert support.

4. Substantially pure pigmentation associated gp 70 antigen specific to melanocytes and melanomas, said antigen having an isoelectric point of 5.2, isolated from melanoma cells.

5. Method of isolating the pigment-associated gp 70 antigen specific to melanocytes and melanomas, said antigen having an isoelectric point of 5.2, comprising immunoprecipitation of a melanoma cell extract with antibodies which specifically bind to said pigment associated gp 70 antigen specific to melanocytes and melanomas and separating said immunoprecipitate from said extract.

6. Method of claim 5 wherein said melanoma cell extract is radiolabelled and said immunoprecipitation is radioimmunoprecipitation.

7. Pigmentation associated gp 70 antigen specific to melanocytes and melanomas, said antigen having an isoelectric point of 5.2, isolated by the method of claim 6.

8. Method of claim 6 wherein said melanoma cell extract is extracted from cultured melanoma cell line SK-MEL-28.

9. Method for detecting pigmented melanoma cells comprising:
   (a) contacting a biological sample containing said cells with antibody of claim 1; and
   (b) detecting the reaction between the cells and the antibody.

10. Method of claim 9 wherein said biological sample is excised tissue.

11. Method of claim 9 wherein said biological sample is excised tumor.

12. Method of claim 9 wherein said biological sample is blood or urine from an individual suspected of having melanoma.

13. Method for detecting pigmented melanoma cells in the serum of an individual comprising:
   (a) contacting said serum with antibody which specifically binds to the pigmentation associated gp 70 antigen specific to melanocytes and melanomas, said antigen having an isoelectric point of 5.2, and
   (b) detecting the reaction between the cells and the antibody.

14. Method for detecting cells in an early stage of differentiation comprising:
   (a) contacting said cells with antibody which specifically binds to the pigmentation associated gp 70 antigen specific to melanocytes and melanomas having an isoelectric point of 5.2; and
   (b) detecting binding between the cells and the antibody.

* * * * *